United States Patent [19]

Hopp et al.

[11] Patent Number: 5,105,005
[45] Date of Patent: Apr. 14, 1992

[54] ALKADIENENITRILES, PROCESS FOR THEIR PREPARATION AND THEIR USE

[75] Inventors: Rudolf Hopp; Thomas Thielmann, both of Holzminden; Wilhelm Göttsch, Bevern, all of Fed. Rep. of Germany

[73] Assignee: Haarmann & Reimer GmbH, Holzminden, Fed. Rep. of Germany

[21] Appl. No.: 581,488

[22] Filed: Sep. 12, 1990

[30] Foreign Application Priority Data

Sep. 28, 1989 [DE] Fed. Rep. of Germany ....... 3932325

[51] Int. Cl.$^5$ ............................................ C07C 255/07
[52] U.S. Cl. ........................................ 558/462; 512/6
[58] Field of Search ..................... 558/462, 374; 512/6

[56] References Cited

U.S. PATENT DOCUMENTS

| 3,325,369 | 6/1967 | Somerville et al. | 512/6 X |
| 3,531,510 | 9/1970 | Blumenthal | 512/6 X |
| 3,655,722 | 4/1972 | Mitchell et al. | 558/462 |
| 3,692,851 | 9/1972 | Henrick et al. | 558/462 |
| 3,700,717 | 10/1972 | Kappeler et al. | 558/462 X |
| 3,842,128 | 10/1974 | Schwarz et al. | 558/462 X |
| 3,960,923 | 6/1976 | DeSimone | 512/6 X |
| 4,156,690 | 5/1979 | DeSimone | 558/462 X |
| 4,193,934 | 3/1980 | Bauer et al. | 512/6 X |
| 4,277,377 | 7/1981 | Webb et al. | 512/6 |

FOREIGN PATENT DOCUMENTS 0017396 10/1981 European Pat. Off. .
0686692 1/1953 United Kingdom .

*Primary Examiner*—Joseph P. Brust
*Attorney, Agent, or Firm*—Sprung Horn Kramer & Woods

[57] ABSTRACT

The invention relates to new alkadienenitriles of the formula

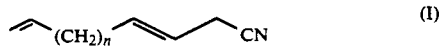

(I)

in which n is an integer from 5 to 9, a process for their preparation and their outstanding suitability as odoriferous substances.

1 Claim, No Drawings

ALKADIENENITRILES, PROCESS FOR THEIR PREPARATION AND THEIR USE

The invention relates to new alkadienenitriles, a process for their preparation and their use as odoriferous substances.

New alkadienenitriles of the formula

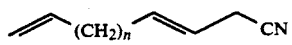  (I)

in which n is an integer from 5 to 9, preferably 7 to 9, which have valuable sensorial properties have been found.

The alkadienenitriles of the formula (I) according to the invention are obtained by condensation of alkenals of the formula

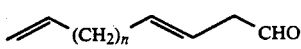  (II)

in which n has the meaning given under formula (I), with cyanoacetic acid.

The invention therefore also relates to a process for the preparation of alkadienenitriles of the formula (I), which is characterized in that alkenals of the formula (II) are subjected to a condensation reaction with cyanoacetic acid in the presence of N,N-dimethylbenzylamine in an inert solvent, such as aromatic hydrocarbons, preferably toluene, at the reflux temperature. The $\alpha,\omega$-alkadienenitrile (mixture of cis and trans isomers) formed in small amounts (<20% by weight) as a by-product in the reaction does not have to be separated off, since it does not impair the olfactory properties of the $\beta,\omega$-alkadienenitriles of the formula (I) according to the invention.

The $\beta,\omega$-alkadienenitriles according to the invention are obtained in form of a mixture of the cis and trans isomers. The weight ratio of the cis and trans isomers varies between 1.5 to 1:1 in dependency from the reaction conditions. The cis and trans isomers differ somewhat in their fragrance notes, but a separation is not required for their use as fragrance.

The alkenals of the formula (II) required as starting substances are commercial products or can be prepared by known processes (see A. J. A. van der Weerdt et al. in "Progress in Essential Oil Research" W. d. Gryter, Berlin 1986, page 215).

The new alkadienenitriles of the formula (I) according to the invention are odoriferous substances which on the one hand have the stability and good persistence of the known nitriles, such as, for example, tridecenenitrile (see British Patent Specification 686, 692), but on the other hand differ from these by a more favourable olfactory note, that is to say a substantially more natural note. Surprisingly, they lack the unpleasant metallic secondary note of the known nitriles.

Examples of some olfactory descriptions are thus: 3, 12-tridecadienenitrile. (mixture of isomers):
fresh citrus/mandarin-like, natural, slightly fruity, very fragrant, cis-3, 12-tridecadienenitrile:
intensive mandarin note;

trans-3, 12-tridecadienenitrile:
less intensive mandarin note but more smooth, flowery, somewhat fatty;

3, 13-tetradecadienenitrile (mixture of isomers):
very fragrant, fruity, waxy, nutty with a note of overripe mandarins or oranges, good persistence.

The odoriferous substances according to the invention are used in combination with other odoriferous substances (Arctander, Perfume and Flavor Chemicals, Montclair, N.J. (USA), 1969) and essential oils (Arctander, Perfume and Flavor Materials of natural Origin, Elisabeth, N.J. (USA), 1960) which are known per se and give perfume bases and odoriferous substance compositions with expressive notes which are outstandingly suitable for perfuming finished products in the aerosol, detergent and chemical industry sector, but especially the fine perfumery and cosmetics sector, for example for detergents, hair care agents, bubble baths, bath salt, washing-up liquids, washing powders, soaps, antiperspirant, powders, creams, shaving lotion, aftershave lotions, air fresheners, WC cleaners, room sprays, antiperspirant sprays, deodorant sprays, body sprays and sunscreen agents.

The odoriferous substances according to the invention are in general employed in these preparations in an amount of 0.001 to 1% by weight, preferably 0.01 to 0.5% by weight, based on the finished preparation.

The perfume compositions and perfumed products are prepared in the customary manner, for example by combining the components.

EXAMPLE 1

168 g (1 mol) of 10-undecenal, 135 g (1 mol) of N,N-dimethylbenzylamine, 93 g (1.1 mol) of cyanoacetic acid and 20 g of water are heated at the reflux temperature in 300 ml of toluene in a three-necked flask fitted with a stirrer, water separator and gas meter, water being separated off. About 25 l of $CO_2$ and 37 g of water are separated off in the course of 60 minutes. The cooled reaction mixture is washed in succession with 250 g of 10% strength sulphuric acid and 250 g of 5% strength sodium bicarbonate solution. The residue which remains after the toluene has been removed is distilled at 107 to 135° C. under 1 mbar. 113 g of 3.12-tridecadienenitrile (mixture of isomers) having a boiling range of 114–116° C. (2 mbar) are obtained. 3, 11-Dodecadienenitrile (mixture of isomers) (boiling point:90° C./1 mbar) and 3, 13-tetradecadienenitrile (mixture of isomers) are obtained by replacing the 10-undecenal by an equivalent amount of 9-decenal or 11-dodecenal respectively.

EXAMPLE 2

An odoriferous substance composition is prepared by mixing the following constituents (amounts in grams):

| | |
|---|---|
| n-decanal | 20.0 |
| trimethylundecylenealdehyde | 2.0 |
| decyl acetate | 100.0 |
| cis-3-hexenol | 2.0 |
| isotridecyl acetate | 80.0 |
| linalyl acetate | 50.0 |
| terpinyl acetate | 50.0 |
| citral | 2.0 |
| 3,12-tridecadienenitrile (mixture of isomers) | 2.0 |
| orange oil (brasilian) | 400.0 |
| α-methyl β-naphthyl ketone | 50.0 |
| limonene | 200.0 |
| ethyl butyrate | 2.0 |
| diethyl phthalate | 48.0 |
| ionol | 2.0 |

By addition of 3, 12-tridecadienenitrile (mixture of isomers), the composition is given a fuller fragrance and in particular a greater naturalness.

Example 3

An odoriferous substance composition is prepared by mixing the following constituents (amounts in grams):

| | |
|---|---|
| 10-undecenal | 2.0 |
| galbanum resin | 10.0 |
| linalyl acetate | 90.0 |
| dihydromyrcenol | 200.0 |
| 3,12-tridecadienenitrile (mixture of isomers) | 2.0 |
| | 1010.0 |

| | |
|---|---|
| orange oil (brasilian) | 90.0 |
| cabreuva oil | 20.0 |
| citronellol | 50.0 |
| benzyl acetate | 150.0 |
| ylang ylang oil | 10.0 |
| benzyl salicylate | 20.0 |
| iraldein | 80.0 |
| 4-tert.-butylcyclohexyl acetate | 60.0 |
| patchouli oil | 20.0 |
| cyclopentadecanolide | 30.0 |
| musk ketone | 30.0 |
| dipropylene glycol | 136.0 |
| | 1000.0 |

The use of 3, 11-tridecadienenitrile (mixture of isomers) also has the effect of a fuller fragrance and a greater naturalness in this composition.

What is claimed is:

1. 3, 12-Tridecadienenitrile.

* * * * *